United States Patent
Wu et al.

(10) Patent No.: US 9,949,946 B2
(45) Date of Patent: Apr. 24, 2018

(54) INCLUSION COMPLEXES OF PINOCEMBRIN WITH CYCLODEXTRIN OR ITS DERIVATIVES

(75) Inventors: Song Wu, Beijing (CN); Guanhua Du, Beijing (CN); Yan Qi, Beijing (CN); Mei Gao, Beijing (CN); Qingyun Yang, Beijing (CN); Hongmei Guang, Beijing (CN); Wei Li, Beijing (CN); Yuehua Wang, Beijing (CN); Yuanfeng Tong, Beijing (CN)

(73) Assignee: CSPC ZHONGQI PHARMACEUTICAL TECHNOLOGY (SHIJIAZHUANG) CO., LTD., Shijiazhuang, Hebei (CN)

(*) Notice: Subject to any disclaimer, the term of this patent is extended or adjusted under 35 U.S.C. 154(b) by 29 days.

(21) Appl. No.: 13/128,602

(22) PCT Filed: Nov. 11, 2008

(86) PCT No.: PCT/CN2008/073011
§ 371 (c)(1),
(2), (4) Date: May 10, 2011

(87) PCT Pub. No.: WO2010/054507
PCT Pub. Date: May 20, 2010

(65) Prior Publication Data
US 2011/0218173 A1    Sep. 8, 2011

(51) Int. Cl.
| | |
|---|---|
| *A61K 47/48* | (2006.01) |
| *A61K 31/352* | (2006.01) |
| *A61K 9/00* | (2006.01) |
| *A61K 9/08* | (2006.01) |
| *B82Y 5/00* | (2011.01) |
| *A61K 47/69* | (2017.01) |

(52) U.S. Cl.
CPC .......... *A61K 31/352* (2013.01); *A61K 9/0019* (2013.01); *A61K 9/08* (2013.01); *A61K 47/6951* (2017.08); *B82Y 5/00* (2013.01)

(58) Field of Classification Search
CPC ............................... A61K 47/48161
USPC ....................................................... 514/58, 54
See application file for complete search history.

(56) References Cited

U.S. PATENT DOCUMENTS

| 5,120,546 A | * | 6/1992 | Hansen et al. ................. 424/449 |
| 2006/0018860 A1 | * | 1/2006 | Chen et al. ................. 424/70.14 |

FOREIGN PATENT DOCUMENTS

| CN | 1424112 A | 6/2003 |
| CN | 1695608 A | 11/2005 |
| CN | 1711992 A | 12/2005 |
| CN | 1739537 A | 3/2006 |
| CN | 1879656 A | 12/2006 |
| JP | 9234005 A | 9/1997 |
| KR | 20060040226 A | 5/2006 |

OTHER PUBLICATIONS

Deng, CN 1415292 A, May 7, 2003.*
Wei Chunhua (English Language Translated Copy (by ProQuest Dialog), CN 1879656 A, pp. 1-7, Dec. 20, 2006).*
Zhang Juntian, Modern Experimental Methods in Pharmacology, Oct. 1998, the First Edition, the United Press of Beijing Medical University and Peking Union Medical College Related Part; I. Regional Cerebral Ischemia Model; 1. Middle Cerebral Artery Occlusion (MCAO) in the Rat. (see Document 3).*
Synthesis of 5,7-dihydroxyflavanone, Cheng Yong-hao, Duan Ya-bo, Oi Yan, Guo Xiao-yun, Tong Yuan-feng, Du Guan-hua, Wu song, Haxue Shiji, 2006, 28 (7), 437-438.
Effects of Compounds Found in Propolis on *Streptococcus mutans* Growth and on Glucosyltransferase Activity, Hyun Koo, Pedro L. Rosalen, Jaime A. Cury, Yong K. Park, and William H. Bowen, Antimicrob, Agents & Chemother. 2002, 46(5), 1302-1309.

* cited by examiner

*Primary Examiner* — Shaojia Anna Jiang
*Assistant Examiner* — Everett White
(74) *Attorney, Agent, or Firm* — Shumaker, Loop & Kendrick, LLP; James D. Miller

(57) ABSTRACT

Inclusion complexes of pinocembrin with cyclodextrin or its derivatives and their preparation are provided. The inclusion complexes can be used to make drugs.

6 Claims, 3 Drawing Sheets

INCLUSION COMPLEXES OF PINOCEMBRIN WITH CYCLODEXTRIN OR ITS DERIVATIVES

TECHNICAL FIELD

The present invention relates to an inclusion complex of pinocembrin with cyclodextrin or its derivative, to a preparation process thereof, to a pharmaceutical composition containing the same, and to a use of said inclusion complex or said pharmaceutical composition.

BACKGROUND OF THE INVENTION

Pinocembrin, known as 5,7-Dihydroxyflavanone or 2,3-Dihydro-5,7-dihydroxy-2-phenyl-4H-1-benzopyran-4-one, is a water insoluble flavanone compound with the following formula:

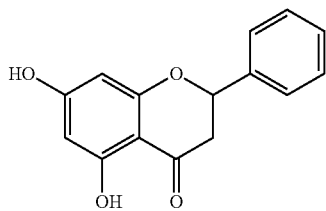 [SMILES: O=C1CC(c2ccccc2)Oc2cc(O)cc(O)c21]

There is one chiral center in the structure of pinocembrin, and natural pinocembrin is in its S-configuration with $[\alpha]_D^{15}$ being −45.3 (c, 0.9, acetone as solvent).

(S)-pinocembrin is a natural product extracted from propolis. It is also found in nut pines, eucalyptus leaves, acacia gum, and the like with low concentrations (*Combined Chemical Dictionary* 2004). Now pinocembrin can be obtained by synthesis and therefore in abundance (Yonghao Cheng, Yabo Duan, Yan Qi, Xiaoyun Guo, Yuanfeng Tong, Guanhua Du, Song Wu, *chemical reagent,* 2006 Vol. 28, No. 7:437).

It is reported in the literature that pinocembrin is sensitive to plenty of malignant bacteria and fungus, and shows a relatively good antibacterial effect especially on some drug resistant strains (Hyun Koo, Pedro L. Rosalen, Jaime A. Cuiy, Yong K. Park, and William H. Bowen, *Antimicrob. Agents & Chemother.* 2002, 46 (5), 1302-1309). CN200410037860.9 discloses Levo-pinocembrin has a good effect on cerebral apoplexy.

Pinocembrin has a low oral bioavailability for its water-insolubility and its relatively low oral absorption. Moreover, it is difficult to make it into an injection for its water-insolubility. Especially since the pharmaceutical formulations are required to release active agents quickly and exert effects rapidly when they are used to treat an acute disease such as cerebral apoplexy, the most common clinical method to treat the acute disorder is an intravenous injection. Therefore, solubility problem of pinocembrin must be solved first in order to obtain injectable dosage forms.

So it is urgent to obtain pharmaceutical formulations of pinocembrin with good water-solubility.

DISCLOSURE OF THE INVENTION

The inventors of the present invention have surprisingly found that the water-solubility of pinocembrin can be enhanced greatly by using cyclodextrin or its derivative to form an inclusion complex of pinocembrin.

Therefore the present invention provides an inclusion complex of pinocembrin with cyclodextrin or its derivative. The inclusion complex comprises pinocembrin and cyclodextrin or its derivative at any ratio. Preferably, the molar ratio of pinocembrin to cyclodextrin or its derivative is in the range of 1:1~1:100, and more preferably is in the range of 1:1~1:10.

In another aspect, the present invention provides a method to make the inclusion complex of pinocembrin with cyclodextrin or its derivative.

The present invention also provides a pharmaceutical composition comprising said inclusion complex of pinocembrin with cyclodextrin or its derivative and optionally a pharmaceutically acceptable carrier or excipient.

The present invention further provides a use of an inclusion complex of pinocembrin with cyclodextrin or its derivative or a pharmaceutical composition containing the inclusion complex for preventing and/or treating a disease or disorder in a subject. In one embodiment, said disease is cardiovascular or cerebrovascular disease or cerebral apoplexy or bacteria and/or fungus infection.

ILLUSTRATION OF FIGURES

Figure 3:
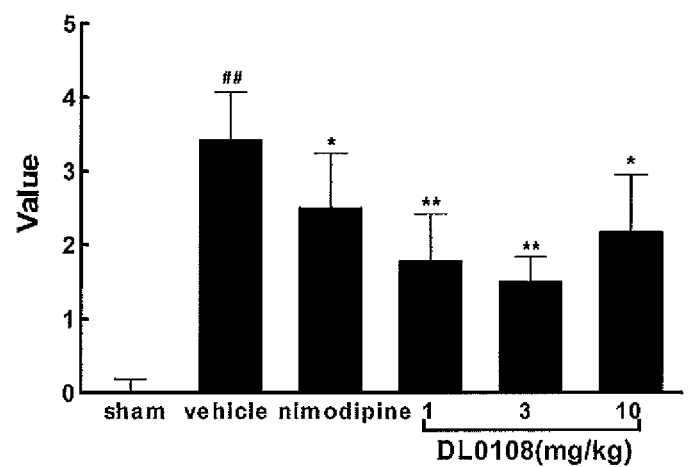
FIG. 3 shows an effect of DL0108 (the inclusion complex of pinocembrin with hydroxypropyl-β-cyclodextrin) on the Bederson score of the MCAO operation-injured rats.
Figure 4:
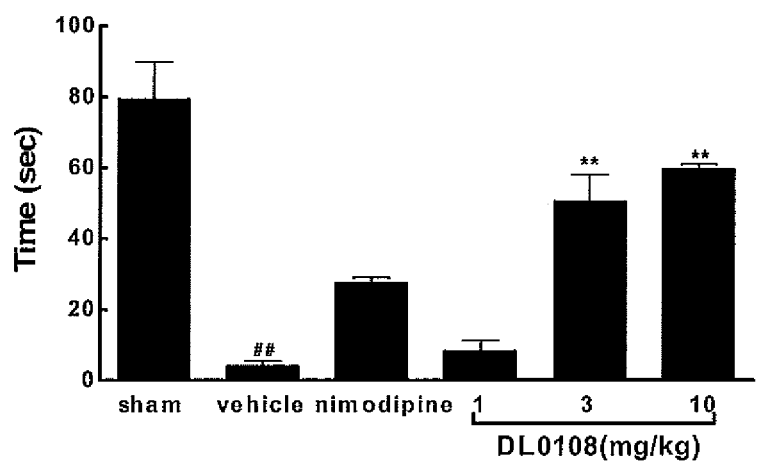
FIG. 4 shows an effect of DL0108 on neurological symptom score (NSS) of the MCAO operation-injured animals.
Figure 5:
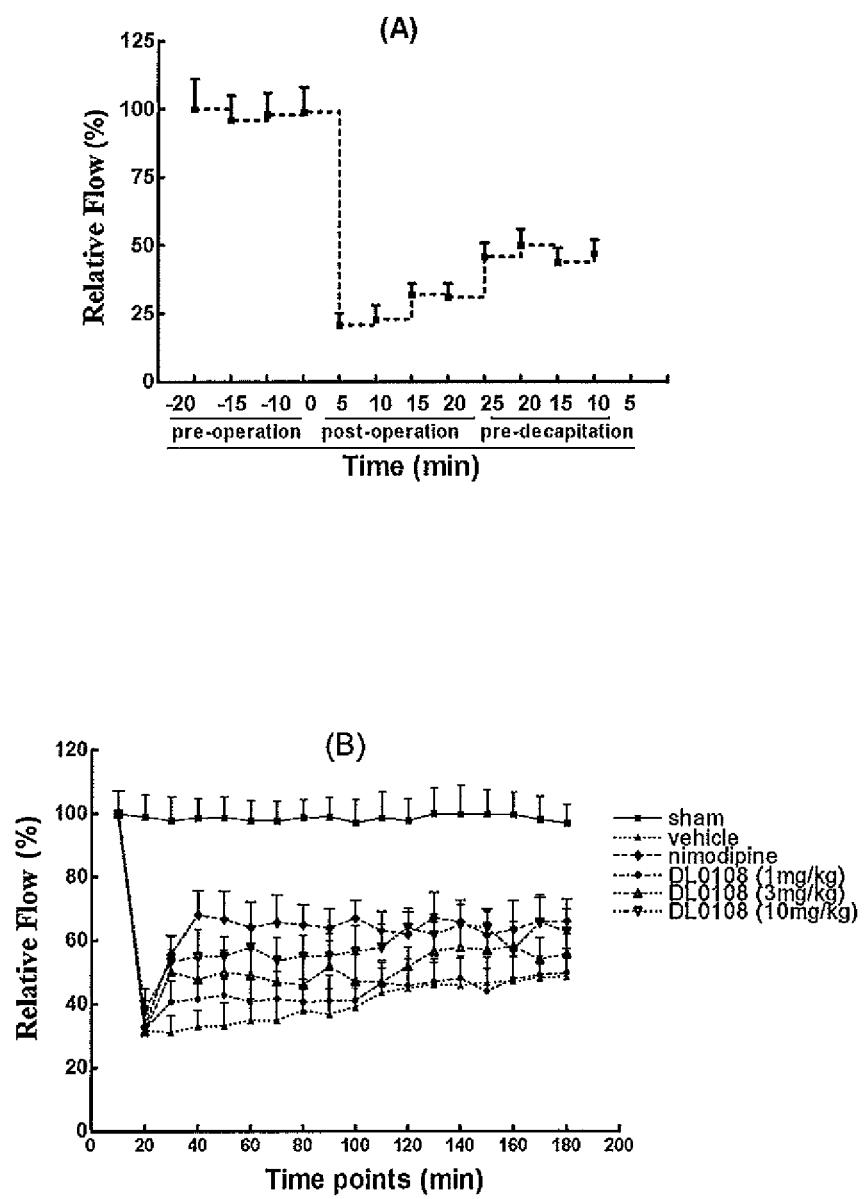
FIG. 5 shows the rCBF (regional cerebral blood flow) value in the cortex medium-sized arterial blood-supplying area at various times after the MCAO operation-injury (A), and the effect of DL0108 on the rCBF value of the MCAO operation-injured rats (B).

The data of FIG. 3~FIG. 5 are expressed as the Average ±S.E.M. The results are analyzed with One-way ANOVA and Dunett's test. N=10, ##P<0.01 vs. the blank control group, *P<0.05, **P<0.01 vs. the vehicle control group.

THE DETAILED DESCRIPTION OF THE PRESENT INVENTION

In one aspect, the present invention provides an inclusion complex of pinocembrin with cyclodextrin or its derivative, wherein said inclusion complex comprises pinocembrin and cyclodextrin or its derivative, and the molar ratio of pinocembrin to cyclodextrin or its derivative is in the range of 1:1~1:100, preferably 1:1~1:10.

In the present invention, the term "pinocembrin" includes L-pinocembrin, S-pinocembrin, racemic pinocembrin, or any combination thereof. Pinocembrin can be obtained from nature resources or by chemical syntheses.

In the present invention, cyclodextrin or its derivative can be selected form the group consisting of α-cyclodextrin, β-cyclodextrin, γ-cyclodextrin, and its derivative having various substituting groups, including but not limited to hydroxyethyl-β-cyclodextrin, dimethyl-β-cyclodextrin, hydroxypropyl-β-cyclodextrin, dihydroxypropyl-β-cyclodextrin, methyl-β-cyclodextrin, glucose cyclodextrin, maltose cyclodextrin, maltotriose cyclodextrin, carboxymethyl cyclodextrin, sulfobutyl cyclodextrin, sulfobutylether-β-cyclodextrin and any combination thereof. In one embodiment, said cyclodextrin or its derivative is β-cyclodextrin or hydroxypropyl-β-cyclodextrin. In another embodiment, said cyclodextrin or its derivative is dimethyl-β-cyclodextrin, hydroxypropyl-β-cyclodextrin, sulfobutylether-β-cyclodextrin, hydroxyethyl-β-cyclodextrin or any combination thereof.

In the present invention, the inclusion complex of pinocembrin with cyclodextrin or its derivative can be in a liquid or solid form or even in a semisolid form, which depends on the requirement of the formulated dosage form or the treatment application.

In another aspect, the present invention provides a pharmaceutical composition comprising an effective amount of said inclusion complex of pinocembrin with cyclodextrin or its derivative and optionally a pharmaceutically acceptable carrier or excipient. Particularly a unit dosage of the pharmaceutical composition contains 1~1000 mg, preferably 50~250 mg of active agent pinocembrin. The inclusion complex of pinocembrin with cyclodextrin or its derivative can be manufactured into proper pharmaceutical composition forms for mammals especially for human with the methods well known by those skilled in the art.

The pharmaceutical composition can be applied in various routes, such as oral administration and intravenous, intramuscular, peritoneal or subcutaneous injection.

The pharmaceutical composition can be prepared into a liquid dosage form such as an injection (including a transfusion, an injectable aqueous solution and an injectable powder), an oral solution and a syrup by using said inclusion complex of pinocembrin with cyclodextrin or its derivative in a liquid form; the pharmaceutical composition can be prepared into a solid dosage form such as a tablet, a capsule, a granule, a dispersible tablet, an orally disintegrating tablet, a buccal tablet and the like by using said inclusion complex of pinocembrin with cyclodextrin or its derivative in a solid form.

The preferable liquid dosage form comprises an injection of the inclusion complex of pinocembrin with hydroxypropyl-β-cyclodextrin, such as an injectable aqueous solution thereof. In one embodiment, said injectable aqueous solution has a concentration of 0.01~3% (g/ml), and a pH of 3~10, preferably 4~9, more preferably 5~8, and especially 6~8; the injectable aqueous solution can further comprise an osmotic pressure regulatory agent such as sodium chloride and glucose, and a pH regulatory agent such as hydrochloric acid and sodium hydroxide.

Said injection can also be in a form of the injectable powder. In one embodiment, a solution in which said injectable powder is dissolved has a pH of 3~10; said injectable powder can further comprise a support agent such as mannitol and lactose, and a pH regulatory agent such as hydrochloric acid and sodium hydroxide.

In another aspect, the present invention provides a process for preparing said inclusion complex of pinocembrin with cyclodextrin or its derivative, comprising the steps of adding cyclodextrin or its derivative into solvent or vehicle to obtain a solution or suspension of cyclodextrin or its derivative with a weight concentration of 1~60%, and preferably 5~60%; adding pinocembrin to said solution or suspension; and mixing by stirring or grinding to obtain said liquid inclusion complex of pinocembrin with cyclodextrin or its derivative. The liquid inclusion complex of pinocembrin with cyclodextrin or its derivative can be a solution or a suspension; the solution of the inclusion complex of pinocembrin with cyclodextrin or its derivative can be obtained when stirring to a clear and transparent state.

A solid inclusion complex of pinocembrin with cyclodextrin or its derivative is obtained by removing the solvent from the solution of the inclusion complex of pinocembrin with cyclodextrin or its derivative for example by lyophilizing, spray drying or distillation-concentration.

In the process for preparing the solid inclusion complex of pinocembrin with cyclodextrin or its derivative, the solution of the inclusion complex of pinocembrin with cyclodextrin or its derivative can firstly be concentrated to a concentration of cyclodextrin or its derivative in range of 10~15% by weight, followed by lyophilizing, to obtain the solid inclusion complex of pinocembrin with cyclodextrin or its derivative.

In one embodiment of the present invention, the solid inclusion complex of pinocembrin with cyclodextrin or its derivative can be obtained by adding cyclodextrin or its derivative into a colloid mill or a mortar, adding an appropriate amount of solvent and stirring to form a paste, adding pinocembrin into said paste, grinding for 1~5 hours to form a viscous paste, followed by filtering, concentrating or lyophilizing.

The suitable solvent capable of dissolving cyclodextrin or its derivative is selected form the group consisting of water, ethanol, methanol, propanol, isopropanol, ethylene glycol, glycerin, acetone, or any combination thereof. Preferably, the solvent is water.

In the above mentioned preparation processes, said pinocembrin can be added as a solid of pinocembrin or a solution of pinocembrin being dissolved in an appropriate amount of organic solvent.

In another aspect, the present invention relates to a use of the inclusion complex of pinocembrin with cyclodextrin or its derivative for the preparation of a pharmaceutical drug for preventing and/or treating the disease or disorder.

In an embodiment, said disease or disorder is a cardiovascular or cerebrovascular disease. In a preferable embodiment, said cardiovascular or cerebrovascular disease is cerebral apoplexy. In another embodiment, said disease or disorder is a bacteria and/or fungus infection.

Moreover, the present invention provides a method for preventing and/or treating a disease or disorder in a subject, which comprises administrating an effective amount of the pharmaceutical composition to the subject in need thereof. The subject can be a mammal, such as cat, dog, horse, sheep, cattle, monkey, orangutan, and the like, and preferably human. In one embodiment, said disease or disorder is a cardiovascular or cerebrovascular disease, especially cerebral apoplexy. In another embodiment, said disease or disease is a bacteria and/or fungus infection. With respect to the effective amount of the pharmaceutical composition in the present invention, it is easy to be determined by a skilled person in the art by a conventional method, and for example it can be 0.001 mg~10 mg/kg of the body weight of the subject. Moreover, the administration route of said pharmaceutical composition can be selected as appropriate, including oral administration or parenteral administration (including intravenous, intramuscular, peritoneal or subcutaneous injection).

With the embodiments of the present invention, the following beneficial effects can be obtained.

Through using cyclodextrin or its derivative to include pinocembrin and make pinocembrin molecules entrap in the tubular structure of cyclodextrin or its derivative, and therefore obtain the inclusion complex of pinocembrin with cyclodextrin or its derivative, the water-solubility of pinocembrin is enhanced greatly. It is determined that at 25° C., the water-solubility of the inclusion complex of pinocembrin with hydroxypropyl-β-cyclodextrin is as high as 2000 mg/100 ml and is much higher than the water-solubility of the pinocembrin without inclusion. The specific results are shown in Example 10.

With the inclusion complex of pinocembrin with cyclodextrin or its derivative of the present invention, the active pinocembrin, in a form of inclusion complex, can be directly used into a solid or liquid dosage form. Cyclodextrin or its derivative is a water-soluble pharmaceutical adjuvant with a low toxicity, and the inclusion complex of pinocembrin with cyclodextrin or its derivative made therefrom is suitable for preparation into various liquid or solid dosage forms. The inclusion complex of pinocembrin with cyclodextrin or its derivative of the present invention has a good water-solubility and a low vaso-irritation, and is suitable for preparation into liquid dosage forms. With the embodiments of the present invention, the problem, such as a low water-solubility of pinocembrin, and an impossibility of direct application in liquid dosage forms especially in injectable dosage forms, have been solved. Moreover, for the enhanced water-solubility, the solid dosage form made therefrom shows a fast disintegration, a good dissolution and a high bioavailability, and is suitable for clinical use.

Moreover, the inclusion complex of the present invention possesses a good security. An acute toxicity test shows that the inclusion complex of pinocembrin with cyclodextrin has an $LD_{50}$ value for mouse intravenous injection of greater than 700 mg/kg, which is 100 times higher than the effective dosage. Safety tests (local blood vessel irritation test, hemolysis test, anaphylaxis test and intramuscular injection local irritation test) show that the inclusion complex of the present invention possesses no irritation to blood vessel, no hemolysis and anaphylaxis, and a very low intramuscular injection local irritation. Therefore the inclusion complex is safe and suitable for preparation into injectable dosage forms.

Pharmacological assay shows that the inclusion complex of pinocembrin with cyclodextrin of the present invention can greatly improve the neurobehavioral injury induced by the acute focal cerebral ischemia in rats, and relieve the decreasing degree of the cerebral blood flow in the cortex medium-sized arterial blood-supplying area. The inclusion complex of the present invention can be prepared into a pharmaceutical drug for preventing and/or treating cardiovascular or cerebrovascular disease, preferably cerebral apoplexy.

It is known in the art that pinocembrin is sensitive to plenty of malignant bacteria and fungus, and shows a relatively good antibacterial effect especially on some drug resistant strains. Therefore the inclusion complex of pinocembrin with cyclodextrin or its derivative can also be used to prepare for a pharmaceutical drug for preventing and/or treating bacteria and/or fungus infection.

Examples set forth below are illustrative of the present invention and are not intended to limit, in any way, the scope of the present invention. Various modifications, conversions or replacements, which may be made by those skilled in the art without departing from the spirit and scope of the invention, are included within the scope of the invention.

Example 1

Preparation of a Liquid Inclusion Complex of Pinocembrin with Hydroxypropyl-β-Cyclodextrin (Solution)

(1) Weighing 40 g hydroxypropyl-β-cyclodextrin, adding it into 400 ml distilled water and dissolving with stirring;

(2) Separately weighing 1 g pinocembrin, adding it into 20 ml absolute ethyl alcohol to form a solution and adding it into said hydroxypropyl-β-cyclodextrin solution to form a mixed solution; and (3) Magnetically stirring the mixed solution at 40-50° C. for 20 minutes to obtain a clear and transparent solution of the inclusion complex of pinocembrin with hydroxypropyl-β-cyclodextrin.

Example 2

Preparation of a Solid Inclusion Complex of Pinocembrin with Hydroxypropyl-β-Cyclodextrin Steps (1)-(3) were identical to those of Example 1.

(4) Lyophilizing the obtained solution of the inclusion complex of pinocembrin with hydroxypropyl-β-cyclodextrin to obtain a solid inclusion complex of pinocembrin with hydroxypropyl-β-cyclodextrin.

Example 3

Preparation of a Solid Inclusion Complex of Pinocembrin with Hydroxypropyl-β-Cyclodextrin (1) Weighing 20 g hydroxypropyl-β-cyclodextrin into a mortar, to which adding 100 ml distilled water and grinding into a paste;

(2) Separately weighing 3 g pinocembrin, adding it into 20 ml absolute ethyl alcohol to form a solution, and adding it into said hydroxypropyl-β-cyclodextrin paste to form a mixed solution; and (3) Grinding the mixed solution for 2 hours to form a homogenous paste, filtering, and evaporating to dryness in vacuum to obtain a solid inclusion complex of pinocembrin with hydroxypropyl-β-cyclodextrin.

Example 4

Preparation of a Sodium Chloride Transfusion of the Inclusion Complex of Pinocembrin with Hydroxypropyl-β-Cyclodextrin (1) Weighing 20 g hydroxypropyl-β-cyclodextrin, adding it into 200 ml distilled water and dissolving with stirring, adding 0.5 g active carbon for injection, heating to 80° C. with stirring, insulating for 15 minutes, and filtering to remove active carbon;

(2) Separately weighing 2 g pinocembrin, adding it into 20 ml absolute ethyl alcohol to form a solution and adding it into said hydroxypropyl-β-cyclodextrin solution to form a mixed solution;

(3) Magnetically stirring the mixed solution at 40-50° C. for 20 minutes to obtain a clear and transparent solution of the inclusion complex of pinocembrin with hydroxypropyl-β-cyclodextrin;

(4) Supplementing water to reach a volume of 800 ml, adding 7-8 g sodium chloride for injection, adjusting the pH to 8-9, and adjusting the pH to 3.5-7 with 0.05 M of HCl or 0.05 M of NaOH, supplementing water to reach a volume of 1000 ml, adding 0.1 g active carbon for injection and stirring for 20 minutes; and (5) Removing active carbon, filling the solution into bottles, and autoclaving at 115° C. for 30 minutes.

Example 5

Preparation of a Glucose Transfusion of the Inclusion Complex of Pinocembrin with Hydroxypropyl-β-Cyclodextrin Steps (1)-(3) were identical to those of Example 4;

(4) Weighing 50 g glucose for injection, adding water with stirring to dissolution to reach a volume of 100 ml, adding 0.1 g active carbon and heating to boil slightly for 15 minutes, and filtering to remove active carbon;

(5) Adding the glucose solution into the inclusion complex solution, supplementing water to reach a volume of 800 ml, adjusting the pH to 6-7 with 0.05 M of HCl or 0.05 M of NaOH, supplementing water to reach a volume of 1000 ml, adding 0.1 g active carbon for injection and stirring for 20 minutes;

(6) Filtering the solution coarsely and finely with a filter and filter sticks (pore size of 1.0 µm, 0.45 µm and 0.22 µm) and filling the solution into bottles, autoclaving at 115° C. for 30 minutes.

Example 6

Preparation of a Sterile Injectable Powder Using the Inclusion Complex of Pinocembrin with Hydroxypropyl-β-Cyclodextrin (1) Weighing 40 g hydroxypropyl-β-cyclodextrin in a sterile operation room, dissolving it into water to reach a volume of 80 ml, adding 0.1 g active carbon, heating to boil slightly for 15 minutes and filtering to remove active carbon;

(2) Separately weighing 1 g pinocembrin, dissolving it into 20 ml absolute ethyl alcohol, adding the solution into said hydroxypropyl-β-cyclodextrin inclusion complex solution;

(3) Magnetically stirring the mixture at 40-50° C. for 20 minutes to obtain a clear and transparent solution of the inclusion complex of pinocembrin with hydroxypropyl-β-cyclodextrin;

(4) Supplementing water to reach a volume of 100 ml, filtering through 0.22 µm membrane, filling into 10 ml vials (2-3 ml per vial), lyophilizing and capping to obtain the sterile injectable powder.

Example 7

Preparation of an Inclusion Complex of Pinocembrin with β-Cyclodextrin

Weighing 40 g β-cyclodextrin, adding it into 100 ml distilled water, heating to 40-50° C. to dissolve β-cyclodextrin. Adding 1 g pinocembrin dissolved in 20 ml absolute ethyl alcohol, magnetically stirring for 2-3 hours, filtering and lyophilizing to obtain the inclusion complex of pinocembrin with β-cyclodextrin.

Example 8

Preparation of an Oral Capsule of the Inclusion Complex of Pinocembrin with β-Cyclodextrin Weighing 20 g of the inclusion complex of pinocembrin with β-cyclodextrin, and mixing it with 80 g lactose by an equivalent doubling method, dissolving into water with HPMC as binder to produce a soft material, granulating the soft material with a 20-mesh sieve, drying at 60° C. to produce dry granules, sorting the dry granules with a 30-mesh sieve, checking up intermediate products; filling into capsules with 50 mg of active agents per capsule, checking up samples and packaging.

Example 9

Preparation of an Oral Tablet of the Inclusion Complex of Pinocembrin with β-Cyclodextrin Weighing 20 g of the inclusion complex of pinocembrin with β-cyclodextrin, mixing it with 80 g lactose and 5 g sodium carboxymethyl starch by an equivalent doubling method, dissolving into water with HPMC as binder to produce a soft material, granulating the soft material with a 20-mesh sieve, drying at 60° C. to produce dry granules, sorting granules with a 30-mesh sieve, adding 1 g Gum Arabic, mixing them homogeneously, tabletting with 50 mg active agents per tablet, checking up samples and packaging.

Example 10 Determination of the Solubility of Pinocembrin

In order to screen solubilizer, cosolvent and non-aqueous solvent useful for injection, a series of experiments were conducted with their general dosages respectively to determine the solubilization effect of pinocembrin. The results are shown in Table 1:

TABLE 1

Determination of the solubility of pinocembrin

| solubilizer | Concentration of solubilizer or non-aqueous solvent in water (g/100 ml) | solution clarity | solubility (mg/ml) |
| --- | --- | --- | --- |
| Water | — | Turbid and insoluble | <0.2 |
| Glycerine | 50 | Turbid and insoluble | <1 |
| Ethyl alcohol | 10 | Turbid and insoluble | <1 |
| Propylene glycol | 50 | Turbid and insoluble | <1 |
| PEG400 | 30 | Turbid and insoluble | <1 |

TABLE 1-continued

Determination of the solubility of pinocembrin

| solubilizer | Concentration of solubilizer or non-aqueous solvent in water (g/100 ml) | solution clarity | solubility (mg/ml) |
|---|---|---|---|
| Tween-80 | 1 | Turbid and insoluble | <1 |
| Polyvidone | 1 | Turbid and insoluble | <1 |
| β-cyclodextrin | 1.8 | Clear | >2 |
| Dimethyl-β-cyclodextrin | 10 | Clear | >10 |
| Hydroxypropyl-β-cyclodextrin | 10 | Clear | >10 |
| Sulfobutylether-β-cyclodextrin | 10 | Clear | >10 |
| Hydroxyethyl-β-cyclodextrin | 10 | clear | >10 |

The solubilities in Table 1 are the solubilities of pinocembrin. The results show that the solubility of pinocembrin can be improved greatly with cyclodextrin or its derivative, however other commonly-used surfactants or solubilizer, cosolvent and non-aqueous solvent don't show good solubilization effect of pinocembrin.

Safety Tests

Safety Tests of Animal on the Pinocembrin Inclusion Complex Injection

The pinocembrin inclusion complex injection was prepared by diluting the sodium chloride transfusion of the inclusion complex of pinocembrin with hydroxypropyl-β-cyclodextrin prepared according to Example 4 with 0.9% sodium chloride solution 10 times.

Figure 1:
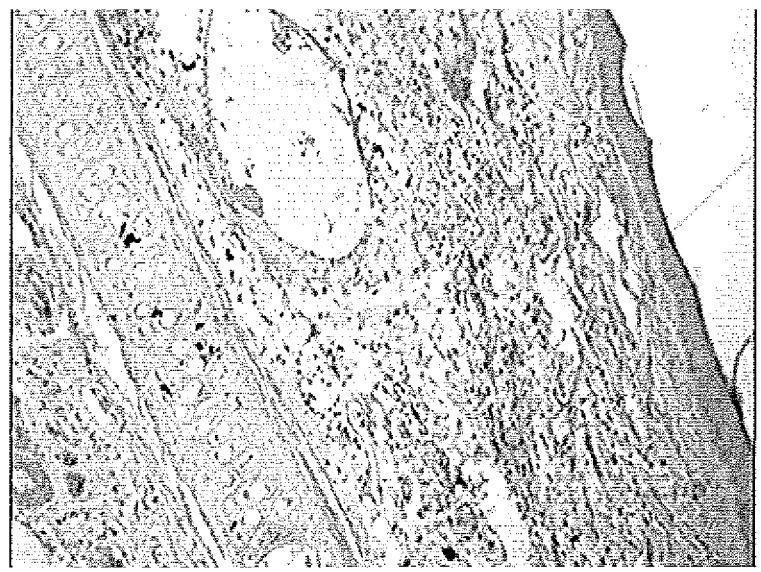
FIG. 1 shows a typical picture of histopathology of rabbit ear injected with normal saline (HE staining). As illustrated in the figure, there is a smooth vein intima without an inflammatory response in the periphery of the blood vessel.
Figure 2:
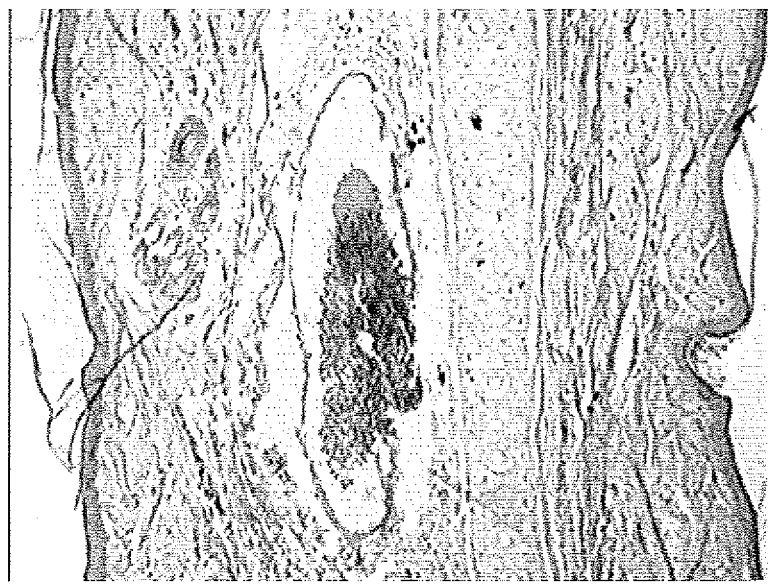
FIG. 2 shows a typical picture of histopathology of rabbit ear injected with the pinocembrin inclusion complex injection (HE staining). As illustrated in the figure, there is a smooth vein intima without an inflammatory response in the periphery of the blood vessel.

1. Local Vascular Irritation Test 10 mL of the pinocembrin inclusion complex injection (containing 2 mg pinocembrin) was given to a rabbit by means of IV injection at the ear vein once daily for 3 d. The injection site and the periphery of the blood vessel were completely and clearly seen without inflammation and irritation response such as reddening or congestion, and had no significant difference from the site injected with normal saline. No abnormal histopathology changes were observed. The results are shown in FIGS. 1 and 2.

2. Hemolysis Test

A red cell suspension, normal saline, various volumes of pinocembrin inclusion complex injections (having a concentration of 0.20 mg/ml) or distilled water were added to 7 tubes according to the formulation listed in Table 2. The tubes were shook slightly to mix well, and then kept in a warm-water bath at 37° C. Hemolysis phenomena were observed at 0.5, 1, 2 and 3 hrs after mixing. There is no significant difference between the results in the tubes containing pinocembrin inclusion complex injections at clinical concentrations and that in the normal saline blank control tube. The results are shown in Table 3.

TABLE 2

Sample distribution list in hemolysis test

| Tube number | 1 | 2 | 3 | 4 | 5 | 6 | 7 |
|---|---|---|---|---|---|---|---|
| 2% red cell suspension (mL) | 2.5 | 2.5 | 2.5 | 2.5 | 2.5 | 2.5 | 2.5 |
| Normal saline (mL) | 2.4 | 2.3 | 2.2 | 2.1 | 2.0 | 2.5 | — |
| Distilled water (mL) | — | — | — | — | — | — | 2.5 |
| pinocembrin inclusion complex injection (0.2 mg/ml) (mL) | 0.1 | 0.2 | 0.3 | 0.4 | 0.5 | — | — |

TABLE 3

Effect of pinocembrin inclusion complex injection on hemolysis

| Times | 1 | 2 | 3 | 4 | 5 | 6 | 7 |
|---|---|---|---|---|---|---|---|
| 0.5 h | − | − | − | − | − | − | + |
| 1 h | − | − | − | − | − | − | + |
| 2 h | − | − | − | − | − | − | + |
| 3 h | − | − | − | − | − | − | + |

Note:
"+" complete hemolysis, "−" no hemolysis.

3. Anaphylaxis Test

The anaphylaxis severity of the guinea pigs, to which a test drug (pinocembrin inclusion complex injection) and a positive control drug (egg albumin) were intravenously administrated for 14 days and 21 days respectively, were observed and determined according to Table 4. The results are shown in Table 5.

TABLE 4

Anaphylaxis criteria

| Grade | Symptoms |
|---|---|
| 0 | No abnormal response |
| 1 | Only a slight nose-scratching, trembling, pilo-erection |
| 2 | Several coughs, with nose-scratching, trembling, pilo-erection |
| 3 | Many or consecutive coughs, with difficult breathing, convulsion, and twitch |
| 4 | convulsion, twitch, gatism, shock, and dead |

TABLE 5

Effect of the pinocembrin inclusion complex injection on active systemic anaphylaxis (ASA) of guinea pigs

| Drug | Grade of anaphylaxis | |
|---|---|---|
| | 14 days | 21 days |
| Test drug (pinocembrin inclusion complex injection) | 0 | 0 |
| Positive control drug (egg albumin) | 4 | 4 |

4. Local Irritation Response Test for the Intramuscular Injection

The severity of the muscle response was determined in accordance with Table 6. At 48 hours after the pinocembrin inclusion complex injection was injected to rabbits, only a slight congestion (diameter <0.5 cm) and no significant irritation response occurred in the injection site with a irritation response average grade lower than 2.0. This demonstrates that the intramuscular injection of the pinocembrin inclusion complex injection has a low local irritation. The results are shown in Table 7.

TABLE 6

The criteria of muscle response

| Grade | Symptoms |
|---|---|
| 0 | No significant difference observed at the injection sites between test drug and control drug |
| 1 | A slight congestion in the muscle site injected with the test drug, smaller than 0.5 × 1.0 cm |
| 2 | A moderate congestion in the muscle site injected with the test drug, larger than 0.5 × 1.0 cm |
| 3 | A severe congestion in the muscle site injected with the test drug with muscle degeneration |
| 4 | A necrosis in the muscle site injected with the test drug, with brown atrophy |
| 5 | An extensive necrosis in the muscle site injected with the test drug |

TABLE 7

Local irritation from the intramuscular injection of the pinocembrin inclusion complex injection

| Group | Number of animals | grade | | | | average grade |
|---|---|---|---|---|---|---|
| normal saline | 4 | 0 | 1 | 1 | 0 | 0.50 |
| pinocembrin inclusion complex injection | 4 | 1 | 0 | 1 | 1 | 0.75 |

Pharmacological Assay

The protection effect of the inclusion complex of pinocembrin with hydroxypropyl-β-cyclodextrin on the acute regional injury of cerebral ischemia in rats Assay Method: The assay was conducted according to the MCAO model method as reported in the literature (Zhang Juntian, Modern Experimental Methods in Pharmacology, October 1998, the First Edition, the United Press of Beijing Medical University and Peking Union Medical College).

Bederson's Score

Animal behavior score of sham operation group was 0. The average value of animal behavior score in the vehicle control group (also called as vehicle group hereinafter) was 3.4±0.6. Most animals showed internal rotation or adduction of the front legs at the opposite side of operation, reduced stretching force while side extrusion to the opposite, twisting or occasional walking in rings, and the behavior score was 3. In addition, a few animals only showed internal rotation of the front legs or reduced resisting force, and the behavior score was 2. Some animals had severe symptoms and lacked autonomic activities, and the behavior score was 4.

The inclusion complexes of pinocembrin with hydroxypropyl-β-cyclodextrin (1 mg/kg, 3 mg/kg, and 10 mg/kg, calculated on the content of the active component pinocembrin, abbreviated as DL0108, similarly hereinafter) can remarkably ameliorate the nerve damage symptoms after the post cerebral ischemia of animals (P<0.05, P<0.01) with a dose-effect relationship and are superior to a positive control of nimodipine (See FIG. 3).

Evaluation of Locomotivity (Inclining Slope Test)

The average time for which the rats stayed on the inclining slope was 79.3±10.4 s in the sham group. In the vehicle group, the average time for which the rats having the acute cerebral ischemia injury stayed on the inclining slope was 4.01±1.42 s, and it was significantly reduced. Compared with the vehicle group, DL0108 (3 mg/kg, 10 mg/kg) could remarkably prolong the time for which the animals stayed on the inclining slope (P<0.01) with a dose-effect relationship. DL0108 (3 mg/kg, 10 mg/kg) are superior to the positive control of nimodipine (FIG. 4).

The effect of DL0108 on rCBF of the rat acute cerebral ischemia tissue.

The rCBF (regional cerebral blood flow) value in the cortex medium-sized arterial blood-supplying area reduced rapidly to 20~30% of the pre-operation basal level because of the MCAO operation. 24 hours after ischemia (pre-decapitation), the collateral circulation compensation established and the rCBF value increased a little compared with the value during the operation, but still below 50% of the basal level. The results are shown in FIG. 5A.

30 minutes after the cerebral ischemia, the rCBF value of the vehicle group was 31.09±5.35% of the basal value, and the rCBF values of the administration groups, i.e., the inclusion complex DL0108 group (1 mg/kg, 3 mg/kg, 10 mg/kg) and the nimodipine group, were 40.76±6.58%, 50.09±7.09%, 53.28±8.03%, 55.58±6.09% of the basal value respectively. The results indicated that the administration groups had a quick recovery in the cerebral blood flow, and showed remarkable improvements over the vehicle group. The DL0108 (3, 10 mg/kg) group and the nimodipine (3 mg/kg) group had significant differences from the vehicle group (P<0.05). The results are shown in FIG. 5B.

In conclusion, the inclusion complex of pinocembrin with hydroxypropyl-β-cyclodextrin of the present invention can greatly improve the neurobehavioral injury induced by the acute focal cerebral ischemia in rats, and relieve the decreasing degree of the cerebral blood flow in the cortex medium-sized arterial blood-supplying area.

The invention claimed is:

1. A solid inclusion complex consisting of pinocembrin and cyclodextrin or its derivative, wherein a molar ratio of the pinocembrin to the cyclodextrin or its derivative is 1:1 to 1:10.

2. The inclusion complex according to claim 1, wherein the pinocembrin is selected from the group consisting of L-pinocembrin, S-pinocembrin, racemic pinocembrin and any combination thereof.

3. The inclusion complex according to claim 1, wherein the cyclodextrin or its derivative is selected from the group consisting of α-cyclodextrin, β-cyclodextrin, γ-cyclodextrin, hydroxyethyl-β-cyclodextrin, dimethyl-β-cyclodextrin, hydroxypropyl-β-cyclodextrin, dihydroxypropyl-β-cyclodextrin, methyl-β-cyclodextrin, glucose cyclodextrin, maltose cyclodextrin, maltotriose cyclodextrin, carboxymethyl cyclodextrin, sulfobutyl cyclodextrin, sulfobutylether-β-cyclodextrin and any combination thereof.

4. The inclusion complex according to claim 1, wherein the solid inclusion complex is prepared by a process comprising the steps of:
 (1) adding the cyclodextrin or its derivative to a solvent to obtain one of a solution and a suspension of the cyclodextrin or its derivative with a weight concentration of 1~60%;
 (2) adding the pinocembrin to the one of the solution and the suspension and mixing by one of stirring and grinding to obtain the inclusion complex, wherein a molar ratio of the pinocembrin to the cyclodextrin or its derivative is 1:1 to 1:10; and (3) removing the solvent to form the solid inclusion complex consisting of pinocembrin with cyclodextrin or its derivative.

5. A process for preparing an inclusion complex, comprising the steps of: (1) adding cyclodextrin or its derivative to a solvent to obtain one of a solution and a suspension of the cyclodextrin or its derivative with a weight concentration of 1~60%; (2) adding pinocembrin to the one of the solution and the suspension and mixing by one of stirring and grinding to obtain the inclusion complex, wherein a molar ratio of the pinocembrin to the cyclodextrin or its derivative is 1:1 to 1:10; and (3) removing the solvent to form a solid inclusion complex consisting of pinocembrin with cyclodextrin or its derivative.

6. The process according to claim 5, wherein the solvent is select form the group consisting of water, ethanol, methanol, propanol, isopropanol, ethylene glycol, glycerin, acetone, and any combination thereof.

* * * * *

UNITED STATES PATENT AND TRADEMARK OFFICE
CERTIFICATE OF CORRECTION

PATENT NO. : 9,949,946 B2
APPLICATION NO. : 13/128602
DATED : April 24, 2018
INVENTOR(S) : Song Wu et al.

Page 1 of 1

It is certified that error appears in the above-identified patent and that said Letters Patent is hereby corrected as shown below:

Please add Assignee INSTITUTE OF MATERIA MEDICA, CHINESE ACADEMY OF MEDICAL SCIENCES residing in XUANWU DISTRICT, BEIJING, CHINA Signed and Sealed this
Nineteenth Day of June, 2018

Andrei Iancu
*Director of the United States Patent and Trademark Office*